United States Patent
Mannino et al.

(10) Patent No.: US 9,620,319 B2
(45) Date of Patent: Apr. 11, 2017

(54) COIL ACTUATOR FOR A SWITCHING DEVICE AND RELATED SWITCHING DEVICE

(71) Applicant: ABB Technology AG, Zürich (CH)

(72) Inventors: Fabio Mannino, Curno (IT); Gabriele Valentino De Natale, Milan (IT)

(73) Assignee: ABB SCHWEIZ AG (CH)

(*) Notice: Subject to any disclaimer, the term of this patent is extended or adjusted under 35 U.S.C. 154(b) by 359 days.

(21) Appl. No.: 14/245,777

(22) Filed: Apr. 4, 2014

(65) Prior Publication Data

US 2014/0218838 A1    Aug. 7, 2014

Related U.S. Application Data

(63) Continuation of application No. PCT/EP2012/067448, filed on Sep. 6, 2012.

(30) Foreign Application Priority Data

Oct. 6, 2011   (EP) .................................. 11184067

(51) Int. Cl.
   *G01R 31/327*    (2006.01)
   *H01H 50/00*     (2006.01)
   (Continued)

(52) U.S. Cl.
   CPC ......... *H01H 50/00* (2013.01); *G01R 31/3278* (2013.01); *H01H 47/10* (2013.01);
   (Continued)

(58) Field of Classification Search
   CPC .... H01H 47/002; H01H 47/009; H01H 50/00; H01H 50/86; H01H 47/00;
   (Continued)

(56) References Cited

U.S. PATENT DOCUMENTS

| | | | | |
|---|---|---|---|---|
| 4,367,510 A | * | 1/1983 | Watanabe | H01H 47/007 307/114 |
| 5,155,521 A | * | 10/1992 | Bell | G03B 9/58 396/240 |

(Continued)

FOREIGN PATENT DOCUMENTS

| JP | 2000-294092 A | 10/2000 |
|---|---|---|
| WO | WO 2011/041482 A1 | 4/2011 |

OTHER PUBLICATIONS

International Search Report (PCT/ISA/210) mailed on Dec. 12, 2012, by the European Patent Office as the International Searching Authority for International Application No. PCT/EP2012/067448.

(Continued)

*Primary Examiner* — Van Trieu
(74) *Attorney, Agent, or Firm* — Taft, Stettinius & Hollister LLP (57) ABSTRACT

An exemplary coil actuator for an associated switching device which can be actuated during its operation from an open position to a closed position to allow a current to flow therethrough and from the closed position to the open position to interrupt such flowing from flowing therethrough. The coil actuator includes a coil electromagnet arranged to move between a rest position and an actuating position, wherein movement from the rest position to the actuating position is suitable to cause the actuation of the switching device; and an electronic component arranged to count an operation time which is indicative of the duration of the actuation of the switching device.

20 Claims, 5 Drawing Sheets

(51) Int. Cl.
*H01H 47/10* (2006.01)
*H01H 83/12* (2006.01)
*H01H 1/00* (2006.01)
*H01H 83/06* (2006.01)
*H01H 83/20* (2006.01)

(52) U.S. Cl.
CPC ........... *H01H 83/12* (2013.01); *H01H 1/0015* (2013.01); *H01H 83/06* (2013.01); *H01H 2083/203* (2013.01)

(58) Field of Classification Search
CPC .... H01H 47/008; H01H 47/22; H01H 50/002; H01H 50/44; Y10T 307/74; Y10T 307/766; Y10T 307/937; Y10T 307/461; Y10T 307/492; Y10T 307/747; Y10T 307/911; Y10T 307/957; Y02B 20/325; G01R 31/327; G01R 31/3271; G01R 31/3277; G01R 31/3278
See application file for complete search history.

(56) References Cited

U.S. PATENT DOCUMENTS

| | | | | |
|---|---|---|---|---|
| 5,345,146 A | * | 9/1994 | Koenck | H05B 33/08 315/169.3 |
| 5,604,656 A | * | 2/1997 | Derrick | H01H 47/002 307/102 |
| 6,554,027 B1 | * | 4/2003 | Schuurman | F16K 31/0655 137/115.09 |
| 6,836,121 B2 | * | 12/2004 | Barbour | H01H 47/325 324/256 |
| 2002/0021540 A1 | | 2/2002 | Opfer et al. | |
| 2005/0225909 A1 | | 10/2005 | Yoshizaki et al. | |
| 2010/0033997 A1 | * | 2/2010 | Crucs | H02H 3/12 363/52 |
| 2011/0080685 A1 | | 4/2011 | Wellner et al. | |

OTHER PUBLICATIONS

Written Opinion (PCT/ISA/237) mailed on Dec. 12, 2012, by the European Patent Office as the International Searching Authority for International Application No. PCT/EP2012/067448.

International Search Report (PCT/ISA/210) mailed on Nov. 21, 2012, by the European Patent Office as the International Searching Authority for International Application No. PCT/EP2012/067451.

Written Opinion (PCT/ISA/237) mailed on Nov. 21, 2012, by the European Patent Office as the International Searching Authority for International Application No. PCT/EP2012/067451.

* cited by examiner

COIL ACTUATOR FOR A SWITCHING DEVICE AND RELATED SWITCHING DEVICE

RELATED APPLICATION

This application claims priority as a continuation application under 35 U.S.C. §120 to PCT/EP2012/067448, which was filed as an International Application on Sep. 6, 2012 designating the U.S., and which claims priority to European Application 11184067.4 filed in Europe on Oct. 6, 2011. The entire contents of these applications are hereby incorporated by reference in their entireties.

FIELD

The present disclosure relates to a coil actuator for a switching device.

BACKGROUND INFORMATION

Known switching devices used in electrical circuits, such as in low or medium voltage electric circuits, such as circuit breakers, disconnectors and contactors, are devices designed to allow the correct operation of specific parts of the electric circuits in which they are installed, and of the associated electric loads. In the context of the present disclosure, the term "low voltage" is referred to applications with operating voltages up to 1000V AC/1500V DC, and the term "medium voltage" is referred to applications in the range from 1 kV to some tens of kilovolt, e.g. 50 kV.

Switching devices can be actuated during their operation from an open position to a closed position to allow a current flowing therethrough and from the closed position to the open position to interrupt such current flowing.

The switching devices include one or more electrical poles, or phases, each having at least a contact movable between a first position, or coupled position, in which it is coupled to a corresponding fixed contact (e.g., switching device in the closed position), and a second position, or separated position, in which it is spaced away from the corresponding fixed contact (e.g., switching device in the open position).

A suitable operating mechanism is operatively associated to the movable contacts to cause the displacement of such movable contacts between the coupled and separated positions.

Coil-based actuators, hereinafter indicated as "coil actuators", are frequently used in switching devices, for example in mechanical operated switching devices for low or medium voltage circuits; mechanically operated switching have an operating mechanism of the known "stored-energy" type, wherein the energy specified for opening the switching device is stored in suitable elastic means, such as springs.

A coil actuator can be used to release mechanical parts of the associated switching device, e.g. corresponding parts of the operating mechanism, so as to open or close the switching device itself, following an opening or a closure command and/or event. Examples of such coil actuators are opening shunt releases, closure shunt releases or undervoltage shunt releases, which are all devices known in the art.

A timing test diagnostic function is requested for evaluating the reliability of the switching device. The timing test diagnostic function measures the time elapsed during the opening operation and/or the closure operation of the switching device.

In known implementations, the timing test diagnostic function is performed by means of various additional equipment which are operatively connected to the switching device and which use the information on the position of the movable contacts, information that is provided for instance by suitable auxiliary contacts.

The additional equipment can include for example: portable instruments for service tasks, IEDs ("intelligent electronic devices") with advanced diagnostic functionalities, electronic protection relays, diagnostic and/or monitoring instruments. The use of such external equipment implies a series of disadvantages, among which: complex wiring and cabling, high installation costs, and encumbrance due to the large volume occupied by the additional equipment.

Therefore, while the known implementations perform satisfactorily, further improvements to this technology are still desired.

SUMMARY

An exemplary coil actuator is disclosed for an associated current switching device which can be actuated during its operation from an open position to a closed position to allow a current flowing therethrough and from said closed position to said open position to interrupt such current flowing, said coil actuator comprising: a coil electromagnet arranged to move between a rest position and an actuating position, wherein the movement from the rest position to the actuating position causes the actuation of said switching device, wherein said coil actuator includes electronic means arranged to count an operation time ($T_{open}$, $T_{close}$) which is indicative of the duration of said actuation of the switching device.

DESCRIPTION OF THE DRAWINGS

Further characteristics and advantages will be more apparent from the description of exemplary, but non-exclusive, embodiments of the coil actuator and the related switching device according to the present disclosure, illustrated in the accompanying drawings, wherein.

It should be understood that in the detailed description that follows, identical or similar components, either from a structural and/or functional point of view, have the same reference numerals, regardless of whether they are shown in different embodiments of the present disclosure; it should also be noted that in order to clearly and concisely describe the present disclosure, the drawings may not be to scale and certain features of the disclosure may be shown in somewhat schematic form.

DETAILED DESCRIPTION

Exemplary embodiments of the present disclosure provide a coil actuator for an associated current switching device which can be actuated during its operation from an open position to a closed position to allow a current flowing therethrough and from the closed position to the open position to interrupt such current flowing.

The coil actuator including: a coil electromagnet arranged to move between a rest position and an actuating position, wherein the movement from the rest position to the actuating position is suitable to cause the actuation of the current switching device; electronic means arranged to count an operation time which is indicative of the duration of the actuation of the switching device.

With reference to the exemplary embodiments of FIGS. 1-5, a coil actuator 1 according to the present disclosure is suitable for being installed in a switching device 100, such as for example a low or medium voltage circuit breaker 100, including at least a pole 101 having one or more movable contacts 102 with associated corresponding fixed contacts 103. The contacts 102 are movable between a coupled position, where they are coupled to the corresponding fixed contacts 103, and a separated position wherein they are spaced away from the corresponding fixed contacts 103.

The current switching device 100 can be actuated during its operation from an open position to a closed position to allow a current flowing therethrough and from the closed position to the open position to interrupt such current flowing. The displacement of the movable contacts 102 from the separated position towards the coupled position allows a current flowing through the coupled movable and fixed contacts 102, 103 (e.g., closure operation of the switching device), and the displacement of the movable contacts from the coupled position towards the separated position causes the interruption of such current flowing (e.g., opening operation of the switching device).

Figure 1:
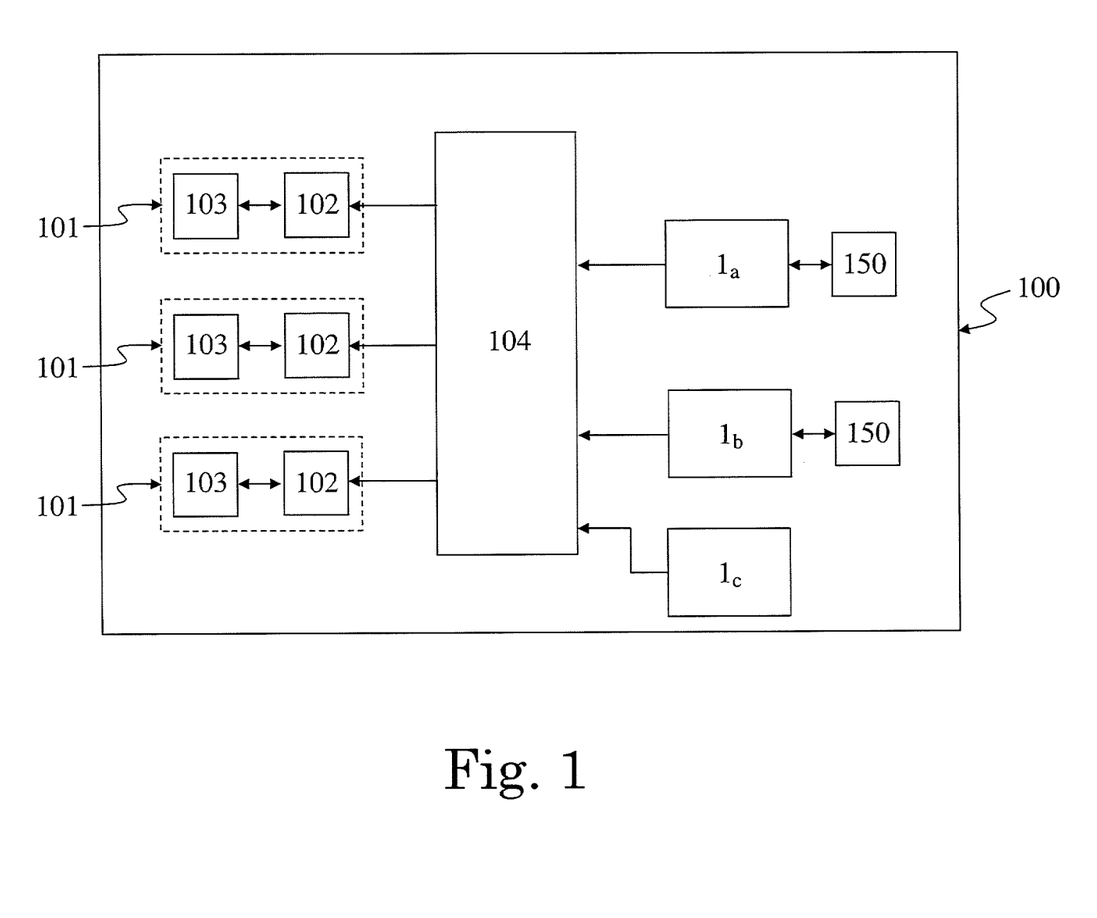
FIG. 1 is a schematic view of a switching device including three coil actuators according to an exemplary embodiment of the present disclosure.

FIG. 1 is a schematic view of a switching device including three coil actuators according to an exemplary embodiment of the present disclosure. FIG. 1 schematically illustrates a switching device 100 having for example three poles 101, each having a movable contact 102 and a corresponding fixed contact 103; such an embodiment has to be understood only as an illustrative and non-limiting example since the principles and technical solutions introduced in the following description can be applied to switching devices 100 having a number of poles 101 different with respect to the illustrate one, such as for example a switching device 100 with a single pole 101, or two poles 101, or four poles 101.

An operating mechanism 104, for example an energy-stored operating mechanism 104, can be operatively connected to the movable contacts 102 to cause the movement of such contacts 102 between the coupled and separated positions with respect to the corresponding fixed contacts 103, and therefore the actuation of the switching device 100 between its closed position and its open position.

The coil actuator 1 includes a coil electromagnet 2 arranged to move between a rest position (or released position) and an actuating position (or launched position), wherein the movement from the rest position to the actuating position is suitable to cause the actuation of the switching 100.

The exemplary coil actuator 1 can be conceived and used in the switching device 100 as a closing actuator 1b, wherein the movement of its coil electromagnet 2 from the released to the launched position causes the closure of the switching device 100, e.g., the actuation of the switching device 100 itself from the open position to the closed position.

The exemplary coil actuator 1 of the present disclosure can be conceived and used in the switching device 100 as an opening actuator 1a, wherein the movement of its coil electromagnet 2 from the released to the launched position causes the opening of the switching device 100, e.g., the actuation of the switching device 100 itself from the closed position to the open position.

Figure 2:
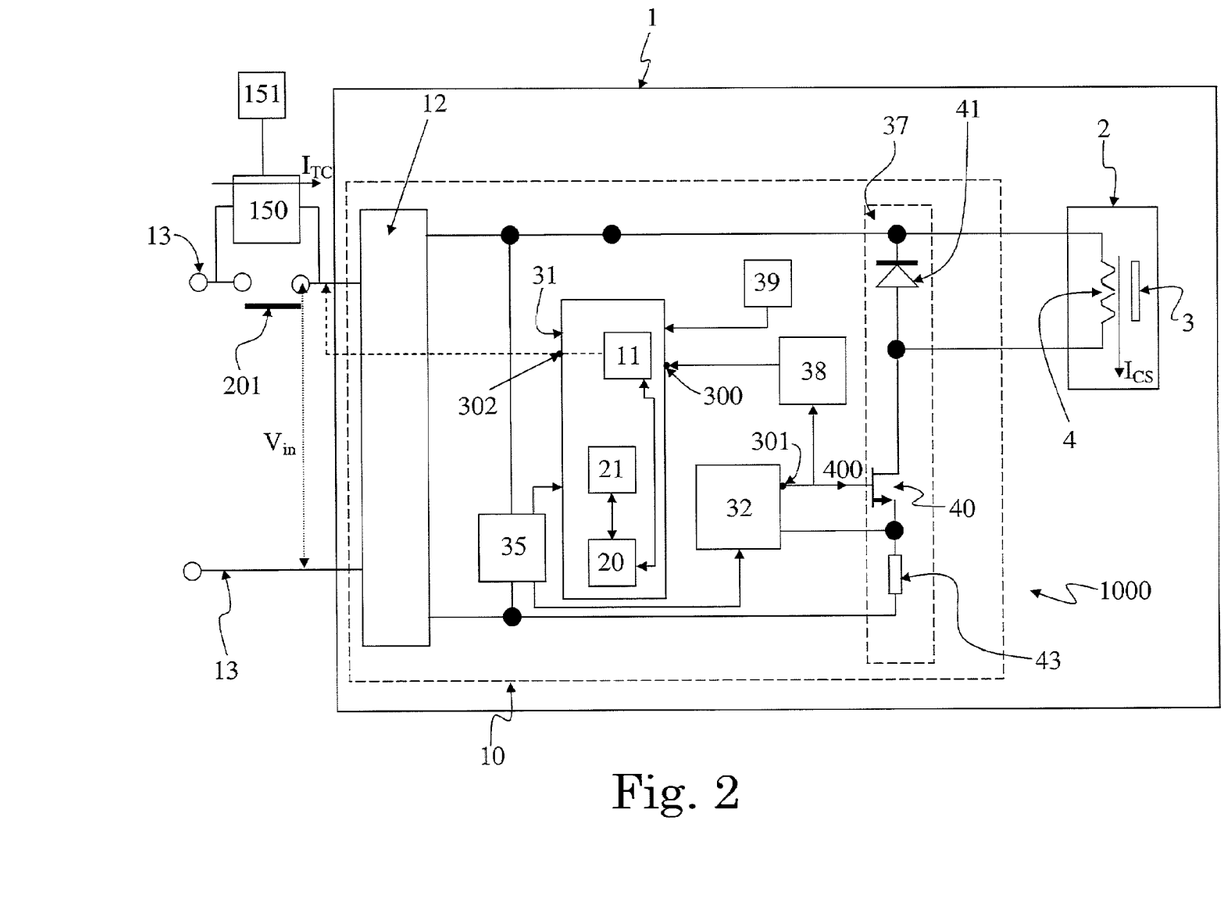
FIG. 2 is a schematic view of a first coil actuator according to an exemplary embodiment of the present disclosure.
Figure 5:
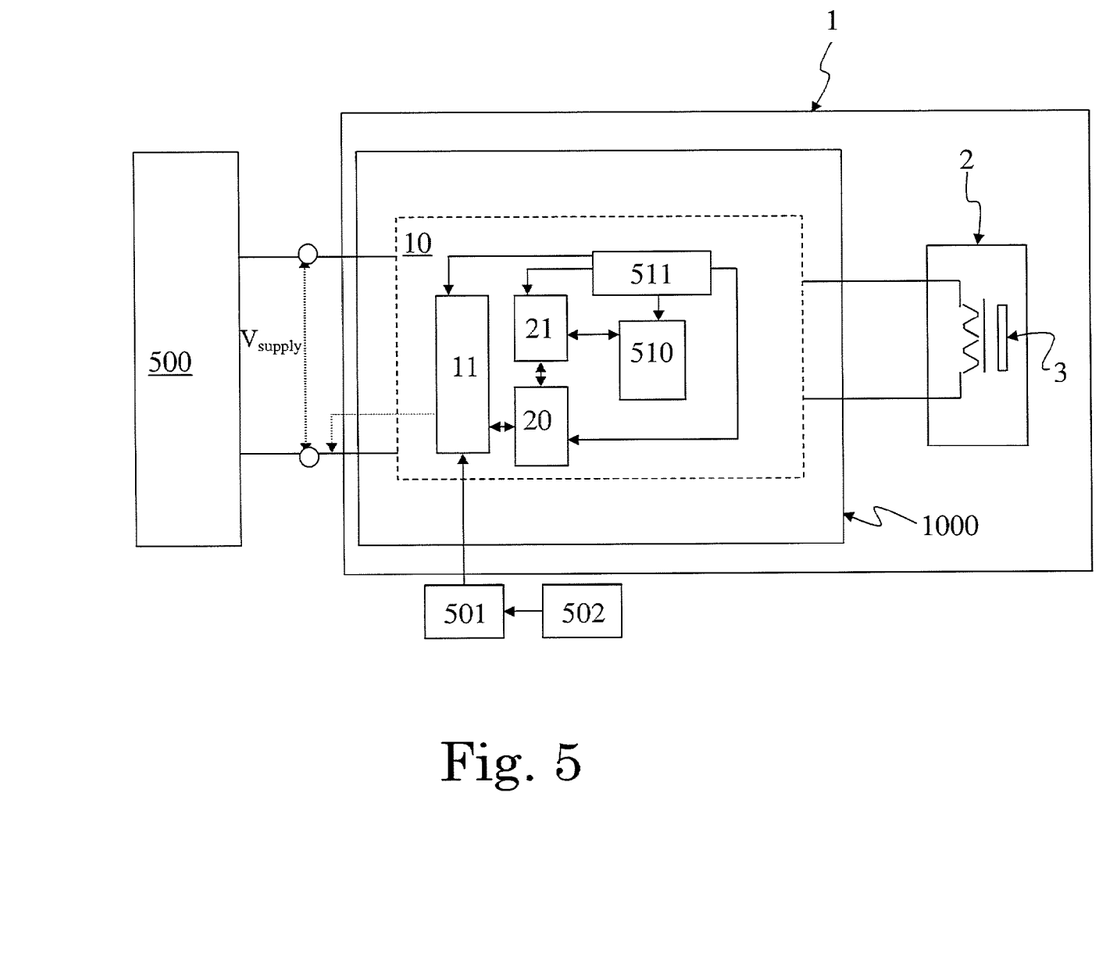
FIG. 5 is a schematic view of a second possible coil actuator according to an exemplary embodiment the present disclosure.

FIG. 2 is a schematic view of a first coil actuator according to an exemplary embodiment of the present disclosure. FIG. 5 is a schematic view of a second possible coil actuator according to an exemplary embodiment the present disclosure. According to an exemplary embodiment of FIG. 2 and to the exemplary embodiment of FIG. 5, the coil electromagnet 2 of the coil actuator 1 includes one or more parts 3 which are arranged to move, during the movement of the coil electromagnet 2 itself from the released to the launched position to interact with one or more corresponding parts of the switching device 100; such operative interaction between the movable parts 3 of the coil electromagnet 2 and the corresponding parts of the switching device 100 causes the actuation of the switching device 100 itself.

According to an exemplary embodiment of the present disclosure, the coil actuator 1 includes for example a case which houses the coil electromagnet 2 and which is configured for allowing a part 3 of the coil electromagnet 2 itself, e.g., an anchor or plunger 3, to move between a first stable position, or retracted position, wherein it is retracted into the case (e.g., coil electromagnet 2 is in the released, or rest, position), and a second stable position, or launched position, wherein at least a portion of the movable part 3 is launched outside the case (e.g., coil electromagnet 2 is in the launched, or actuating, position). The movable part 3 of the coil electromagnet 2 is arranged to release, through its movement from the retracted to the launched position, one or more corresponding mechanical parts of the operating mechanism 104 of the switching device 100 to cause the actuation of the switching device 100.

In accordance with an exemplary embodiment of the present disclosure, the coil actuator 1 can be configured as an opening actuator and installed into the switching device 100 in such a way that the interaction between the movable parts 3 of its electromagnet 2 and the corresponding parts of the switching device 100, e.g., parts of the operating mechanism 104, causes the opening of the switching device 100, e.g., the actuation of the switching device 100 itself from its closed to position to its open position.

In accordance with another exemplary embodiment of the present disclosure, the coil actuator 1 can be configured as a closing actuator and installed into the switching device 100 such that the interaction between the movable parts 3 of its electromagnet 2 and the corresponding parts of the switching device 100, e.g., parts of the operating mechanism 104, causes the closure of the switching device 100, e.g., the actuation of the switching device 100 itself from its open position to its closed position.

For example, the switching device 100 illustrated in FIG. 1 includes at least an opening actuator 1a and a closure actuator 1b.

The coil actuator 1 according to the present disclosure includes electronic means 1000 (e.g., computing device), embedded inside the coil actuator 1 itself, which are arranged to count an operation time which is indicative of the duration of the actuation of the switching device 100, actuation caused by the coil actuator 1 itself.

The opening actuator 1a according to the present disclosure includes electronic means 1000 arranged to count an opening operation time $T_{open}$ which is indicative of the duration of the opening of the switching device 100, e.g., of the actuation of the switching device 100 from the closed position to the open position. According to an exemplary embodiment, the counted opening operation time $T_{open}$ is indicative of the time elapsed during the movement of the contacts 102 of the switching device 100 from their coupled to their separated position with respect to the corresponding fixed contacts 103.

The closing actuator 1b according to the present disclosure includes electronic means 1000 (e.g., computing device) arranged to count a closure operation time $T_{close}$ which is indicative of the duration of the closure of the switching device 100, e.g., of the actuation of the switching device 100 itself from the open position to the closed position. According to an exemplary embodiment, the counted closure operation time $T_{close}$ is indicative of the time elapsed during the movement of the contacts 102 of the switching device 100 from their separated to their coupled position with respect to the corresponding fixed contacts 103.

For example, in the switching device 100 illustrated of FIG. 1, the opening actuator 1a and the closing actuator 1b each include corresponding electronic means 1000 which are arranged to count the opening operation time $T_{open}$ and the closing operation time $T_{close}$ of the illustrated switching device 100, respectively.

In accordance with exemplary embodiments of the present disclosure shown in FIG. 2 and FIG. 5, the electronic means 1000 of the coil actuator 1 according to the present disclosure include: detection means 11 (e.g., sensor) arranged to detect a first event, or launch event, which is indicative of an actuation request or condition of the switching device 100; and driving means 10 (e.g., generator) operatively associated with the detection means 11 and connected to the coil electromagnet 2. The driving means 10 are arranged to electrically drive the coil electromagnet 2 to cause at least the movement thereof from the released position to the launched position upon the detection of the launch event by the detection means 11. The detection means 11 of the coil actuator 1 are also arranged to detect a second event which is indicative of the end of the actuation of the switching device 100, wherein such actuation is caused by the coil actuator 1 itself upon the detection of the launch event and the resulting movement of its coil electromagnet 2.

The electronic means 1000 of the coil actuator 1 further comprise counting means 20 (e.g., counter) which are operatively associated to the detection means 11 and are arranged to start the counting of the operation time ($T_{open}$ for the opening actuator 1a or $T_{close}$ for the closing actuator 1b) when the launch event is detected by the detection means 11, and to stop such counting when the second event is detected by the detection means 11. Therefore, the detection of the launch event and the detection of the second event trigger the start and the end, respectively, of the counting performed by the counting means 20.

The electronic means 1000 of the coil actuator 1 according to the present disclosure includes comparing means 21 (e.g., comparator) operatively associated to the counting means 20 and arranged to compare the counted operation time ($T_{open}$ for the opening actuator 1a or $T_{close}$ for the closure actuator 1) with a temporal acceptance range $T_{range}$ which is indicative of an acceptable value for the operation time. The opening operation time $T_{open}$ has a specified value which depends on the specific applications of the switching device 100, and the closure operation time $T_{close}$ has a specified value which depends on the constructive characteristics of such switching device 100. For instance, the specified opening operation time $T_{open}$ of a mechanically operated medium voltage circuit breaker 100 falls in the range between 50 and 73 ms, while the specified closing operation time $T_{close}$ falls in the range between 50 and 70 ms.

The comparing means 21 can be arranged to receive and store at least a configurable parameter, wherein the configurable parameter can include the desired acceptance temporal range $T_{range}$ for the counted operation time.

The coil actuator 1 can be arranged to cause the generation of an alarm signaling, e.g., the generation of at least an alarm signal and/or indication, when the counted operation time $T_{open}$ or $T_{close}$ exceeds the associated temporal range $T_{range}$.

The driving means 10 can be configured to apply a configurable delay time between the detection of the launch event and the consequent electrical driving of the coil electromagnet 2, wherein such delay time has a duration set to guarantee an accurate desired operation time for the actuation of the switching device 100.

The coil actuator 1 according to the exemplary embodiment of FIG. 2 can be installed and used in the switching device 100 as a shunt opening release (e.g., opening actuator 1a) configured for opening the switching device 100 following an opening command and/or signal, or alternatively can be installed and used in the switching device 100 as a shunt closing actuator (e.g., closing actuator 1b) configured for closing the switching device 100 following a closure command and/or signal.

The opening and closure commands and/or signals can be generated automatically by suitable means or by an operator and can be generated inside the switching device 100 or received by remote. For example, an opening, or trip, command can be generated by a protection device installed into the switching device 100 upon the detection of an electrical fault.

The driving means 10 of the coil actuator 1 according to the exemplary embodiment of FIG. 2 are arranged to electrically drive the coil electromagnet 2 to hold it in the launched position and to allow the return thereof from the launched position to the release position upon the detection of the second event, or release event, by the detection means 11.

Figure 3:
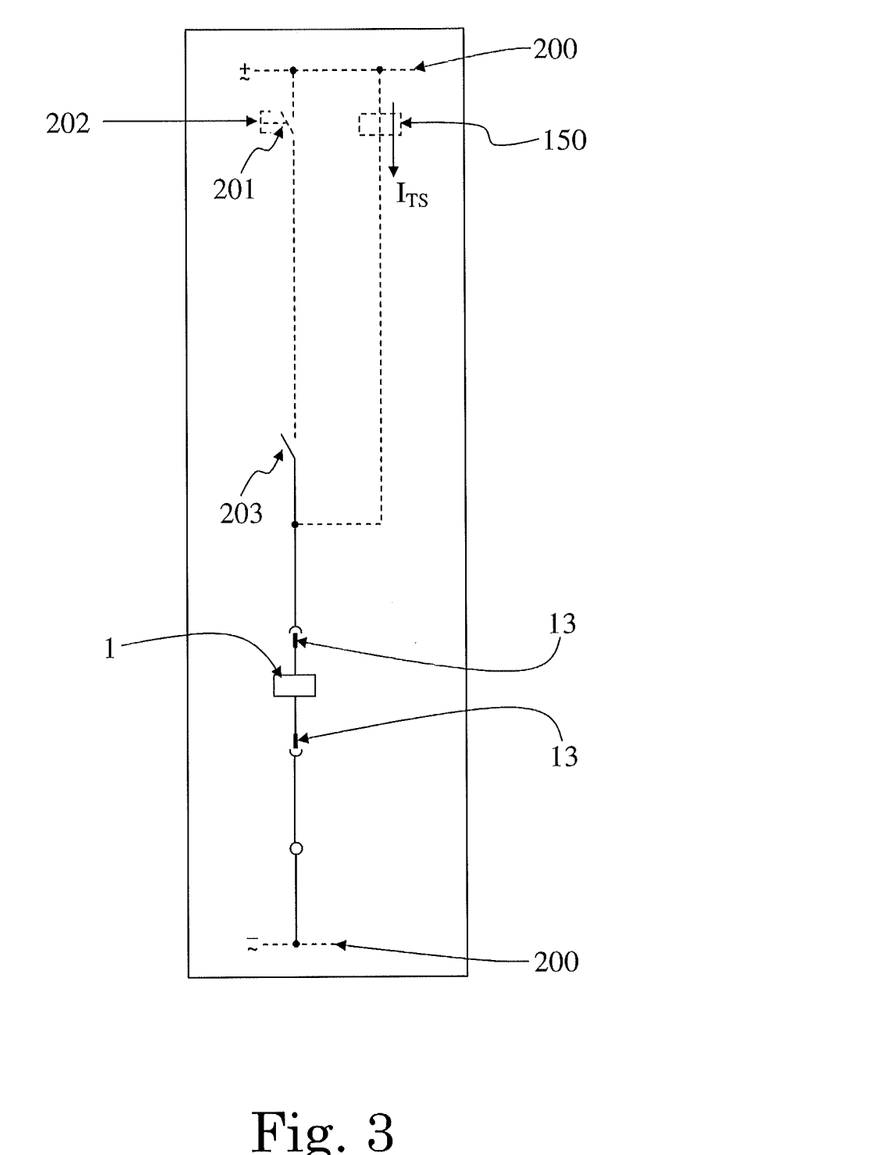
FIG. 3 is a schematic view of a first coil actuator operatively connected to a power supply and to a trip circuit supervisor according to an exemplary embodiment of the present disclosure.

Such driving means 10 includes a power input circuit 12 arranged to be operatively connected to and receive an input voltage $V_{in}$ from at least a power source, e.g., a power associated to the switching device 100 and/or to the electric circuit into which the switching device 100 itself is installed, for example a power line 200 associated to the switching device 100 (see FIG. 3).

The power input circuit 12 can be arranged to use the received input voltage $V_{in}$ to provide a suitable power supply to several components and/or elements of the coil actuator 1, at least to the driving means 10, the counting means 20, the detection means 11 (and the comparing means 21, if present). For instance, the power input circuit 12 may include one or more input filters and a rectifier to convert the AC voltage received from the power line 200 to a DC input voltage.

The detection means 11 can be arranged to continuously sense a voltage indicative of the input voltage $V_{in}$, e.g., to sense directly the voltage $V_{in}$ applied to the power input circuit 12 or indirectly through a voltage generated in the coil actuator 1 and depending on such input voltage $V_{in}$. The detection means 11 are arranged to detect, by means of the sensed voltage, a first threshold value, or launch threshold value $V_{th\_launch}$, and a second threshold value, or release threshold value $V_{th\_release}$, of the input voltage $V_{in}$, wherein the launch threshold value $V_{th\_launch}$ can be higher than the release threshold value $V_{th\_release}$.

The driving means 10 are operatively associated to the detection means 11 to electrically drive the coil electromagnet 2 for moving and holding the coil electromagnet 2 in the launched position upon the detection of the launch threshold value $V_{th\_launch}$. The launch and hold operations of the coil electromagnet 2 can be executed by the driving means 10 using the power drawn from the input voltage $V_{in}$, having a value above the launch threshold value $V_{th\_launch}$.

The driving means 10 can be operatively associated to the detection means 11 to at least reduce, e.g., interrupt, the electrical driving of the coil electromagnet 2 for allowing the return thereof from the launched position to the release position, upon the detection of the release threshold value $V_{th\_release}$ by the detection means 11.

The detection of the launch threshold value $V_{th\_launch}$ and the detection of the release threshold value $V_{th\_release}$ are the launch event and the release event which trigger the start and the end, respectively, of the counting performed by the counting means 20. If the coil actuator 1 of FIG. 2 is installed and used in the switching device 100 as a shunt opening release 1a, the detection of the launch threshold value $V_{th\_launch}$ and the detection of the release threshold value $V_{th\_release}$ are the launch event and the release event which trigger the start and the end, respectively, of the counting of the opening operation time $T_{open}$ of the switching device 100.

If the coil actuator 1 of FIG. 2 is installed and used in the switching device 100 as a closing shunt release (e.g., closing actuator 1b), the detection of the launch threshold value $V_{th\_launch}$ and the detection of the release threshold value $V_{th\_release}$ are the launch event and the release event which trigger the start and the end, respectively, of the counting of the closure operation time $T_{close}$ of the switching device 100.

In the exemplary embodiment of FIG. 2, the coil actuator 1 includes a single coil electromagnet 2, e.g., a coil electromagnet 2 having a single electromagnetic coil 4 operatively associated to the movable part 3 and electrically connected to the driving means 10. The driving means 10 are arranged to: generate a launch current $I_L$ flowing through the electromagnetic coil 4 to generate a magnetic force suitable for moving the part 3 from the retracted to the launched position; consequently reduce and maintain the launch current $I_L$ at a holding current $I_H$ suitable for holding the movable part 3 in the launched position.

The driving means 10 illustrated in FIG. 2 advantageously includes a first control unit 31 and a second control unit 32, wherein the second control unit 32 is suitable for controlling the current flowing through the single coil electromagnet 2 and the first control unit 31 is operatively connected to the second control unit 32 for setting the current which has to flow through the single coil electromagnet 2. By using the single coil electromagnet 2 and the associated first and second control units 31, 32, the number of electromagnetic variables is reduced, therefore reducing the manufacturing and handling costs.

The first control unit 31 can be any electronic device suitable for receiving and executing software instructions and for receiving and generating output data and/or signals through a plurality of input and/or output ports. For example, the controller 31 may be a microcontroller 31, such as the MSP430 microprocessor produced and made available in commerce by Texas Instruments®.

The driving means 10 can include a power circuit 37 operatively connected to the single coil electromagnet 2 and to the second control unit 32 to generate the current flowing through the single coil electromagnet 2 according to the control performed by the second control unit 32. In the embodiment of FIG. 2 the second control unit 32 is for example a PWM ("pulse width modulation") controller 32 and the associated power circuit 37 includes: an electronic power switch 40 to electrically drive the single coil electromagnet 2, such as a power MOSFET ("metal-oxide-semiconductor field-effect transistor"); a freewheeling diode 41; and a sense resistor 43 for measuring the current flowing through the single coil electromagnet 2. In practice, the PWM controller 32 is configured for driving the power switch 40 through a PWM signal 400 to regulate the current flowing through the single coil electromagnet 2 according to the settings received from the control unit 31.

The power input circuit 12 is operatively connected to the power circuit 37, the first control unit 31 and the second control unit 32 to provide them the power specified to operate; for example, a power converter 35 is provided to convert and adapt the voltage outputted by the power input circuit 12 into values suitable for supplying the first and second controllers 31, 32.

The controller 31 stores instructions which, when executed by the controller 31 itself, implement the counting means 20, the detection means 11 and the comparing means 21 of the shunt release (e.g., coil actuator 1). The controller 31 can be arranged to receive and store configurable parameters, for example through a software download operation, including at least the launch and release voltage threshold values $V_{th\_launch}$, $V_{th\_release}$ of the detection means 11, and the temporal range $T_{range}$ of the comparing means 21. A jumper 39 can be operatively connected to the controller 31 to allow the resetting of at least a stored configurable parameter.

In order to implement the detection means 11, an input port 302 of the controller 31 is associated to the implemented detection means 11 and is electrically connected at the electrical point where the input voltage $V_{in}$ is applied to the power input circuit 12 (as shown schematically in FIG. 2), to continuously and directly sense such input voltage $V_{in}$.

Alternatively to the exemplary embodiment of FIG. 2, the coil electromagnet 2 may include two electromagnetic coils, or windings, operatively associated to the movable part 3, wherein the driving means 10 connected to such coil electromagnet 2 would be arranged to selectively energize the two coils for moving the part 3 from the retracted to the launched position and for holding such movable part 3 in the launched position, until a release event is detected by the detection means 11.

With reference to FIG. 3, the power input circuit 12 of the shunt release (e.g., coil actuator 1) illustrated in FIG. 2 is operatively connected to the power source 200 through cables 13 and at least a contact 201 is placed along the power delivery path from the power source 200 to the power input circuit 12 to realize or interrupt such delivery path according to its closure or opening, respectively.

If the coil actuator 1 of FIG. 2 is installed and used in the switching device 100 as an opening shunt release 1a, the closing of the contact 201 is driven by an opening command and/or signal 202. If the coil actuator 1 of FIG. 2 is installed and used in the switching device 100 as a closing shunt release (e.g., closing actuator 1b), the closing of the contact 201 is driven by a closing command and/or signal 202.

For example, the contact 201 may be a contact of a protection relay, closed upon the occurrence of a fault event detected by the protection device itself, or may be a button actuable by an operator.

The electrical connection between the power input circuit 12 and the power supply 200 through the closure of the contact 201 causes the rising of the input voltage $V_{in}$ above the launch threshold value $V_{th\_launch}$, in such a way that the driving means 10 are supplied with the power specified to perform the launch and hold operations of the coil electromagnet 2.

The launch operation of the coil electromagnet 2 causes the opening of the switching device 100 if the coil actuator 1 is installed and used in the switching device 100 as a shunt opening release (e.g., opening actuator 1a), or causes the closure of the switching device 100 if such coil actuator 1 is installed and used in the switching device 100 as a shunt closing release (e.g., closing actuator 1b). Accordingly, the counting means 20 starts to count the operation time ($T_{open}$ for the shunt opening actuator 1a or $T_{close}$ for the shunt closing actuator 1b).

An auxiliary contact 203 is placed along the power delivery path realized by the closure of the contact 201. The auxiliary contact 203 is operatively connected to one or more movable contacts 102 of the switching device 100 to move between an open operative status and a closed operative status according to the movement of contacts 102.

The auxiliary contact 203 is suitable for interrupting the associated delivery path when it moves from its closed to its open status. If the coil actuator 1 of FIG. 3 is installed and used in the switching device 100 as a shunt opening release (e.g., opening actuator 1a), the auxiliary contact 203 is operatively connected to the corresponding movable contacts 102 to be in closed status while the switching device 100 is in its closed position, and to reach its open status at the end of the opening operation of the switching device 100 caused by the shunt opening release (e.g., opening actuator 1a), e.g., when the movable contacts 102 reach their separated position with respect to the corresponding fixed contacts 103.

If the coil actuator 1 of FIG. 3 is installed and used in the switching device 100 as a shunt closing release (closing actuator 1b), the auxiliary contact 203 is operatively connected to the corresponding movable contacts 102 to be in the closed status while the switching device 100 is in its open position, and to reach its open status at the end of the closure of the switching device 100 caused by the shunt closing release (e.g., closing actuator 1b), e.g., when the movable contacts 102 reach their coupled position with respect to the corresponding fixed contacts 103.

FIG. 5 is a schematic view of a second possible coil actuator according to an exemplary embodiment the present disclosure. As shown in FIG. 5, the coil actuator 1 according to the present disclosure can be conceived and installed into the associated switching device 100 to operate as an shunt undervoltage release (e.g., undervoltage actuator 1c), e.g., to intervene for opening and/or the switching device 100 upon the detection of an undervoltage condition.

The electronic means 1000 of the coil actuator 1 according to such embodiment are arranged to count the opening operation time $T_{open}$ indicative of the duration of the actuation of the switching device 100 from its closed to its open position, actuation which is caused by the coil actuator 1 itself upon the detection of an undervoltage condition.

For example, the switching device 100 in FIG. 1 also includes a shunt undervoltage release (e.g., undervoltage actuator 1c) according to the present disclosure, which is suitable for counting the opening operation time $T_{open}$ of the switching device 100 in addition or alternatively with respect to the counting performed by the shunt opening release (e.g., opening actuator 1a).

According to the exemplary embodiment of FIG. 5, the driving means 10 of the electronic means 1000 embedded in the undervoltage shunt release (e.g., undervoltage actuator 1c) can be operatively connected to at least a power source 500 that is associated with the switching device 100 and/or to the electric circuit into which such switching device 100 is installed. The undervoltage shunt release (e.g., undervoltage actuator 1c) is connected to the power source 500 to receive therefrom the power specified to hold the coil electromagnet 2 in its released (or rest) position, e.g. the power specified to keep the movable part 3 of the coil electromagnet in the retracted position against a force generated by compressed elastic means.

The detection means 11 of the electronic means 1000 embedded in the undervoltage release (e.g., undervoltage actuator 1c) are arranged to detect a condition, or event, indicative of the occurrence of the undervoltage condition. For instance, the detection means 11 are arranged to: continuously sense a voltage associated to the power source 500, e.g., to sense directly the supply voltage $V_{supply}$ of the power source 500 or indirectly through a voltage generated in the shunt undervoltage release and depending on such voltage $V_{supply}$; and detect, by means of the sensed voltage, the falling of the supply voltage $V_{supply}$ below a predetermined undervoltage threshold value.

The driving means 10 are arranged to at least reduce, e.g., interrupt, the energizing of the coil electromagnet 2 to cause the movement of the part 3 from the retracted to the launched position upon the detection of the falling of supply voltage $V_{supply}$. The detection of the undervoltage condition by the detection means 11 is the launch event that triggers the start of the counting of the opening operation time $T_{open}$ by means of the counting means 20 provided in the electronic means 1000.

The detection means 11 are also arranged to detect the event indicative of the end of the opening of the switching device 100, opening operation caused by the shunt undervoltage release (e.g., undervoltage actuator 1c); such detection is the event that triggers the end of the counting of the opening operation time $T_{open}$.

For example, the detection means 11 in FIG. 5 are arranged to detect an electrical signal 501 suitable for signaling the end of the opening operation of the switching device 100 caused by an undervoltage condition, such as a signal 501 generated by the closure of a contact 302 operatively connected to one or more of the movable contacts 102 of the switching device 100 so as to close when such one or more movable contacts 102 reach their separated position with respect to the corresponding fixed contacts 103.

The undervoltage shunt release (e.g., coil actuator 1) illustrated in FIG. 5 further includes: the comparing means 21 for comparing the counted opening operation time $T_{open}$ with the temporal range $T_{range}$; and alarm generating means 510 operatively associated to the comparing means 21 and arranged to generate an alarm signal and/or indication if the counted opening operation time $T_{open}$ exceeds the temporal range $T_{range}$.

The coil actuator 1 according to the present disclosure is arranged to provide a continuous power supply to the counting means 20, at least for a time specified to complete the counting operation, wherein such counting operation can include storing the counted operation time ($T_{open}$ for the opening actuator 1a and $T_{close}$ for the closing actuator 1b) in suitable storage means provide in the coil actuator 1. If the comparing means 21 are provided, the coil actuator 1 is also arranged to provide a continuous power supply also to such comparing means 21, at least for a time specified to complete the comparison operation.

For example, the undervoltage shunt release (e.g., coil actuator 1) according to the embodiment of FIG. 5 includes at least a backup capacitor 511 suitable for storing energy drawn by the $V_{supply}$ applied to the undervoltage shunt release 1c and connected at least to the counting means 20 and the comparing means 21 to release the stored energy thereto, starting from the occurrence of the undervoltage condition up to the end of the counting operation and of the comparison operation. The backup capacitor 511 (or alternatively other suitable energy storage means) is also connected to: the detection means 11 to provide them the power specified to detect the signal 501 indicative of the end of the opening operation of the switching device 100, even during the undervoltage condition; and the alarm generating means 510 to provide them the power specified to generate the alarm signaling, even during the undervoltage condition.

According to a first exemplary solution, the coil actuator 1 according to the embodiment of FIG. 2 can include a backup capacitor connected to the power input circuit 12 to be charged while the input voltage $V_{in}$ is applied to the coil actuator 1 itself by the power source 200. Advantageously, the backup capacitor can be the smoothing capacitor used in the power input circuit 12 to rectify the AC voltage received from the power line 200 to a DC input voltage.

With reference to FIG. 3, at the opening of the auxiliary contact 203 the application of the input voltage $V_{in}$ to the power input circuit 2 of the coil actuator 1 stops, and the backup capacitor releases the stored energy to supply the counting means 20 (and the comparing means 21, if provided) to conclude the counting operation (and the comparison operation).

According to a second exemplary solution, the counting means 20 (and the comparing means 21, if provided) of the coil actuator 1 according to the embodiment of FIG. 2 are operatively connected to the power input circuit 12 of the driving means 10. The power input circuit 12 is in turn arranged to be operatively connected to the associated power source 200 so as to receive therefrom the power specified to continuously supply at least a minimum input voltage $V_{in\_min}$ to the counting means 20 (and the comparing means 21, if provided); the minimum input voltage $V_{in\_min}$ is suitable for providing the counting means 20 with the power specified to complete the counting operation (and for providing the comparing means 21 with the power specified to complete the comparison operation).

With reference to FIGS. 2 to 3, the coil actuator 1 is advantageously arranged to be operatively connected a trip circuit supervisor 150 installed into the switching device 100.

The trip circuit supervisor 150 is arranged to check the integrity of the coil electromagnet 2, e.g., the integrity of the electromagnetic coil 4 in the coil actuator 1 illustrated FIG. 2, and of the driving means 10 associated thereto (coil supervision and feedback routine). For example, the trip circuit supervisor 150 may be a supervision relay of the type well known in the art, and therefore not further described herein.

According to the exemplary embodiment of FIG. 2, the power input circuit 12 of the coil actuator 1 is arranged to be operatively connected to the trip circuit supervisor 150 to continuously receive, through such trip circuit supervisor 150, the power specified to supply the minimum input voltage $V_{inmin}$ to the counting means 20, the comparing means 21, and also to the detection means 11 and the driving means 10. For example, the power input circuit 102 in FIG. 2 provides, through the trip circuit supervisor 150, the minimum input voltage $V_{in\_min}$ to the first control unit 31 (implementing the control, counting, detecting and comparing functionalities as previously described), the PWM controller 32, and the power circuit 37. In practice, the input minimum voltage $V_{in\_min}$ is suitable to supply the minimum power specified from the coil actuator 1 to work and perform its functionalities.

With reference to FIG. 3, the trip circuit supervisor 150 is placed along a power delivery path from the power source 200 to the power input circuit 12 of the coil actuator 1, wherein such delivery path is parallel with respect to the power delivery path including the contact 201 and the auxiliary contact 203. In this way, when the contact 201 or the auxiliary contact 203 interrupts the associated power delivery path, the coil actuator 1 remains powered to work through the trip circuit supervisor 150.

The detection means 11 of the coil actuator 1 according to such embodiment are also arranged to detect the minimum input voltage $V_{in\_min}$ and the driving means 10 are arranged to electrically drive the coil electromagnet 2 to generate a coil supervisor current $I_{cs}$ flowing through such coil electromagnet 2 when the input voltage $V_{in}$ is detected to be in the range included between the minimum input voltage $V_{in\_min}$ and the release threshold value $V_{th\_release}$. The coil supervisor current $I_{cs}$ is lower than the currents generated by the driving means 10 to perform the launch and hold operations of the coil electromagnet 2; for example, the supervisor current $I_{cs}$ is lower than the launch current $I_L$ and the hold current $I_H$ flowing through the electromagnetic coil 4 of the coil actuator 1 illustrated in FIG. 2.

The current $I_{tc}$ flowing through the trip circuit supervisor 150 depends on the supervisor current $I_{cs}$ flowing through the coil electromagnet 2; the driving means 10 are arranged to: monitor the current $I_{cs}$ or at least a parameter associated to such current $I_{cs}$; check the integrity of the coil electromagnet 2 basing on such monitoring of the supervisor current $I_{cs}$; at least reduce, for example interrupt, the current $I_{cs}$ upon the checking of a failure in the coil electromagnet 2.

The trip circuit supervisor 150 is configured for: sensing the current $I_{tc}$ flowing therethrough; detecting the reduction of the such current $I_{ts}$ below a first predetermined threshold, wherein the reduction of the current $I_{ts}$ is due to the reduction of the supervisor current $I_{cs}$; and generating an alarm signaling 151 upon such detection.

In the exemplary embodiment of FIG. 2 an input port 300 of the controller 31 is operatively connected to the output 301 of the PWM controller 32 from which the PWM signal 400 is sent to the MOSFET 40; for example, a low pass filter 38 is used to convert the PWM signal 400 into a voltage suitable for being measured by the controller 31.

The controller 31 measures the duty cycle "D" of the PWM signal 400, such duty cycle D depending on the input voltage $V_{in}$, the current set by the controller 31 and the coil impedance of the single coil electromagnet 2 (e.g., the electrical impedance associated to electromagnetic coil 4).

Therefore, the measurement of the duty cycle D provides an indication on the integrity of the single coil electromagnet 2. The controller 31 is configured for comparing the measured duty cycle D to a predetermined acceptance range, for example, a configurable acceptance range, and for changing the current settings sent to the PWM controller 32 to at least reduce, e.g., interrupt, the current $I_{cs}$ flowing through the single coil electromagnet 2 when the measured duty cycle D exceeds the acceptance range.

The current $I_{tc}$ is therefore reduced to activate the alarm signaling 151 of the trip circuit supervisor 150. The current $I_{tc}$ flowing through the trip circuit supervisor 150 can be calculated as follows:

$$Itc = Ics \cdot D + Iq,$$

wherein $I_q$ is a quiescent current, e.g., the current specified by the coil actuator 1 to stay active and work.

Hence, if the supervision current $I_{cs}$ is interrupted by the controller 31 due to a failure in the single coil electromagnet 2, the current $I_{tc}$ is reduced to the quiescent current $I_q$ which has a value below the set first predetermined threshold for activating the alarm signaling 151.

According to the exemplary embodiment of FIG. 2, the comparing means 11 and the driving means 10 of the coil actuator 1 are operatively associated each other (in the coil actuator 1 of FIG. 2 are both implemented by the controller 31), and the driving means 10 are advantageously arranged to at least reduce, e.g., interrupt, the supervisor current $I_{cs}$ when the comparing means 11 detect that the counted operation time ($T_{open}$ for the shunt opening release (e.g., opening actuator 1a) or $T_{close}$ for the shunt closure release 1) exceeds the temporal range $T_{range}$ of the comparing means 21. In this manner, the supervisor current $I_{cs}$ is reduced by the driving means 10 so that the current $I_{tc}$ flowing through the trip circuit supervisor 150 falls below the first predetermined threshold. In this way, such reduction of the supervisor current $I_{cs}$ simulates the detection of a failure in the coil electromagnet 2 and consequently activates the alarm signaling 151 already provided in the trip circuit supervisor 150.

Alternatively, the shunt trip supervisor 150 may be configured for discriminating between a first condition wherein a fault occurs in the supervised coil electromagnet 2 and a second condition wherein the counted operation time ($T_{open}$ or $T_{close}$) exceeds the temporal range $T_{range}$. In this way, the shunt trip supervisor 150 can be arranged to generate two different alarm signaling, one indicative of the first condition and the other of the second condition. For example, the driving means 10 can be arranged to reduce the supervisor current $I_{cs}$ so that the current $I_{tc}$ flowing through the trip circuit supervisor 150 falls below a second predetermined threshold, different with respect to the first threshold, when the comparing means 11 detects that the counted operation time ($T_{open}$ or $T_{close}$) exceeds the temporal range $T_{range}$ of the detection means 11.

If such second threshold is set above the first threshold, the shunt trip supervisor 150 can be arranged to detect when the current $I_{tc}$ which has fallen below the second threshold also falls below the first threshold; if the current $I_{tc}$ falls below also to the first threshold, the trip circuit supervisor 150 is arranged to generate the alarm signaling 151 indicative of a fault in the supervised coil electromagnet 2. If the current $I_{tc}$ does not fall below also to the first threshold, the trip circuit supervisor 150 is arranged to generate an alarm signaling, different to the above mentioned alarm signaling 151, which is dedicate for signaling the exceeding of the temporal range $T_{range}$.

If the second threshold is set below the first threshold, the shunt trip supervisor 150 is arranged to detect when the current $I_{tc}$ which has fallen below the first threshold also falls below the second threshold; if the current $I_{tc}$ falls below also the second threshold, the trip circuit supervisor 150 is arranged to generate an alarm signaling indicative of the exceeding of the temporal range $T_{range}$. If the current $I_{tc}$ does not fall below also to the second threshold, the trip circuit supervisor 150 is arranged to generate the alarm signaling 151 indicative of a fault in the supervised coil electromagnet 2.

The operation of the coil actuator 1 according to the exemplary embodiment of FIG. 2 is now disclosed by making reference to a coil actuator 1 installed and used in the switching device 100 as a shunt opening actuator (e.g., opening actuator 1a) shown in FIG. 1.

It is assumed that the movable part 3 of the single coil electromagnet 2 is in the retracted position. With reference to FIG. 3, it is further assumed that the switching device 100 is in its closed position, the contact 201 is open and the auxiliary contact 203 is closed; therefore the power input circuit 12 of the coil actuator 1 is connected to the power source 200 only through the power delivery path realized through the trip circuit supervisor 150.

Figure 4:
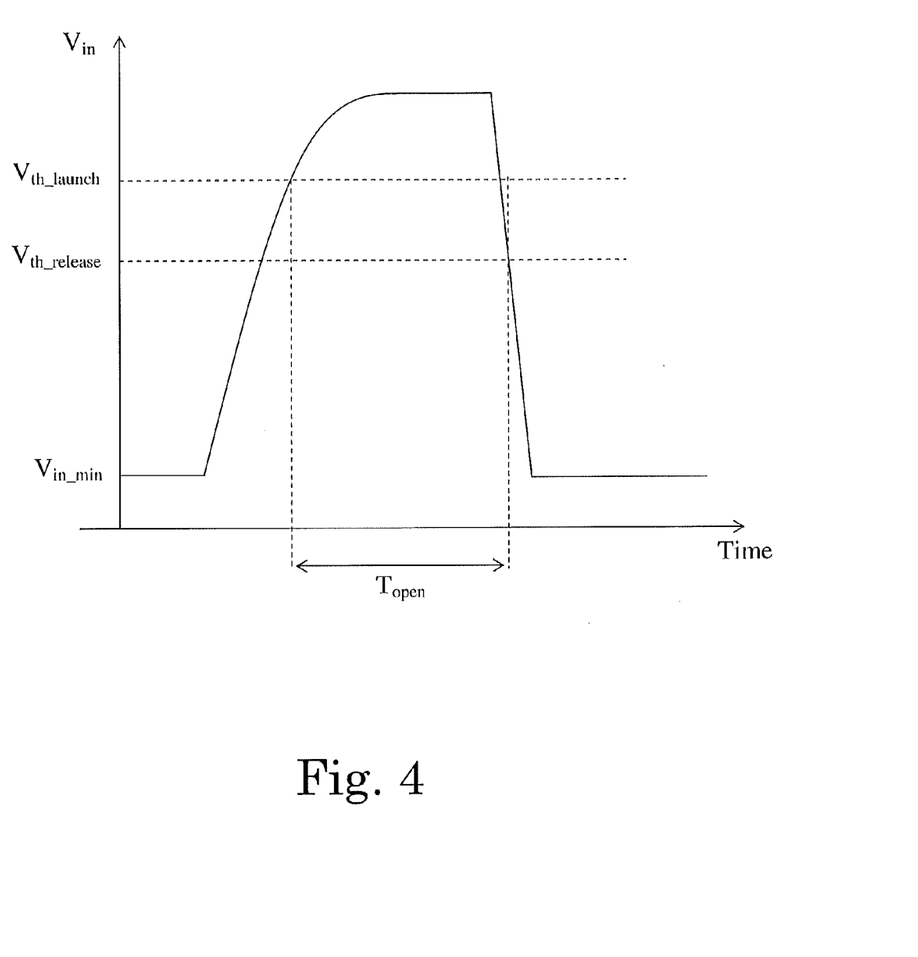
FIG. 4 is a plot showing time dependence of the voltage applied at the input of a first coil actuator in according to an exemplary embodiment of the present disclosure.

The trip circuit supervisor 150 applies to the power input circuit 12 the minimum input voltage $V_{in\_min}$ specified by the controller 31, the PWM controller 32 and the power circuit 37 to stay active and work (see FIG. 4).

Therefore, if the input voltage $V_{in}$ is not below the minimum voltage $V_{in\_min}$ the controller 31 can execute the coil supervision and feedback routine, wherein the controller 31 itself causes, through the PWM controller 32 and the power circuit 36, the flowing of the supervisor current $I_{cs}$ into the single coil electromagnet 2.

During the flowing of the supervisor current $I_{cs}$, the current $I_{ts}$ flows through the trip circuit supervisor 50 and is given by the sum of the quiescent current $I_q$ and a current term depending on the supervisor current $I_{cs}$. If during the execution of the coil supervision and feedback routing the controller 31 checks a failure in the single coil electromagnet 2, through the measured duty cycle D, the current $I_{cs}$ is interrupted by the controller 31 itself, and the current $I_{tc}$ becomes equal to the quiescent current $I_q$ to activate the alarm signaling 151 provided in the trip circuit supervisor 150.

When the opening of the switching device 100 is specified, the opening command and/or signal 202 corresponding to such request is sent to and drives the contact 201 which accordingly moves from its open to its closed status to realize the power delivery path parallel with respect to the path realized through the trip circuit supervisor 150. At the closure of the contact 201 the input voltage $V_{in}$ rises from the minimum input voltage $V_{in\_min}$ above the launch threshold value $V_{th\_launch}$ of the detection means 11 (see FIG. 4).

Upon the detection of the launch threshold value $V_{th\_launch}$ by the detection means 11, the controller 31 causes, through the PWM controller 32 and the power circuit 37, the generation of the launch current $I_L$ to move the movable part 3 of the single coil electromagnet 2 from the retracted to the launched position. After a predetermined launch time, the launch current $I_L$ is reduced to and keep at a holding current $I_H$ suitable for holding the movable part 3 in the launched position. The detection of the launch threshold value $V_{th\_launch}$ is also the event that triggers the start of the counting of the opening operation time $T_{open}$ by the counting means 20 implemented into the controller 31 (see FIG. 4).

The movement of the part 3 of the single coil electromagnet 2 from the retracted to the launched position causes the actuation of the switching device 100 from its closed position to its open position; at the end of such opening operation, i.e. when the movable contacts 102 of the switching device 100 itself reach their separated position with respect to the corresponding fixed contacts 103, the auxiliary contact 203 opens and interrupts the power delivery path associated thereto.

Therefore, at the opening of the auxiliary contact 203 the input voltage $V_{in}$ quickly falls below the release threshold value $V_{th\_release}$ of the detection means 11, until returning to the minimum voltage $V_{in\_min}$ value set by the connection between the power input circuit 12 and the trip circuit supervisor 150 (see FIG. 4).

Upon the detection of the release threshold value $V_{th\_release}$ by the detection means 11, the controller 31 causes, through the PWM controller 32 and the power circuit 37, the reduction of the holding current $I_H$ to the supervisor current $I_{cs}$, to allow the return of the movable part 3 form the launched position to the retracted position and to re-start the execution of the coil supervision and feedback routine. The detection of the release threshold value $V_{th\_release}$ is also the event that triggers the end of the counting of the opening operation time $T_{open}$ by the counting means 20 (see FIG. 4).

When the counting is completed, the counted opening operation time $T_{open}$ is compared to the predetermined temporal range $T_{range}$ of the comparing means 21; if the counted operation $T_{open}$ exceeds such temporal range $T_{range}$, the controller 31 causes, through the PWM controller 32 and the power circuit 37, the interruption of the supervisor current $I_{cs}$ and the consequent reduction of the current $I_{tc}$ of the trip circuit supervisor 150 below the associated threshold to activate the alarm signaling 151 of the trip circuit supervisor 150 itself.

According to an exemplary embodiment of the present disclosure the coil actuator 1 can be installed and used in the switching device 100 as a shunt closing release (e.g., closing actuator 1b).

The movement of the movable part 3 of such shunt closing release 1 from the retracted to the launched position causes the actuation of the switching device 100 from its open position to its closed position.

With reference to FIG. 3, when the closure of the switching device 100 is specified, the closure command and/or signal 202 corresponding to such request is sent to and drives the contact 201 which accordingly moves from its open to its closed status to realize the power delivery path parallel with respect to the path realized through the trip circuit supervisor 150. At the closure of the contact 201, the input voltage $V_{in}$ rises from the minimum input voltage $V_{in\_min}$ above the launch threshold value $V_{th\_launch}$ of the detection means 11.

The detection of the launch threshold value $V_{th\_launch}$ is the event that triggers the start of the counting of the closure operation time $T_{close}$ by the counting means 20.

Further, the auxiliary contact 103 is connected to one or more of the movable contacts 102 of the switching device 100 to open when such movable contacts 103 reach their coupled position with respect to the corresponding fixed contacts 103. Therefore, at the opening of the auxiliary contact 203 the input voltage $V_{in}$ quickly falls below the release threshold value $V_{th\_release}$ of the detection means 11, until returning to the minimum voltage $V_{in\_min}$.

The detection of such falling of the input voltage $V_{in}$ below the release threshold value $V_{th\_release}$ is the event that triggers the end of the counting of the closure operation time $T_{close}$.

Considering the undervoltage shunt release 1c according to the exemplary embodiment of FIG. 5, the supply voltage $V_{supply}$ applied by the power source 500 to the undervoltage shunt release 1c falls below the associated undervoltage threshold when an undervoltage condition occurs.

The falling of the supply voltage $V_{supply}$ below the undervoltage threshold is detected by the detection means 11 and the driving means 10 stops energizing the associated coil electromagnet 2 upon such detection. Hence, the movable part 3 of the coil electromagnet 2 is free to move from the retracted to the launched position for causing the actuation of the switching device 100 from its closed position to its open position. The detection of the falling of the supply voltage $V_{supply}$ below the undervoltage threshold is also the event which triggers the start of the counting of the opening operation time $T_{open}$ by the counting means 20 embedded in the undervoltage shunt release 1c.

After the voltage supply $V_{supply}$ falls due to an undervoltage occurrence, the backup capacitor 511 provides to the detection means 11, the counting means 20, the comparing means 21 and the alarm generating means 510 the energy specified to work.

At the end of the opening operation of the switching device 100 caused by the shunt undervoltage release 1c, the signal 501 is generated, for example by the closure of the corresponding contact 502, which is detected by the detection means 11. Such detection is the event that triggers the stop of the counting of the opening operation time $T_{open}$. If the comparing means 21 detects that the counted time $T_{open}$ exceeds the temporal range $T_{range}$, the alarm generating means 510 generate the alarm signaling 151.

In practice, it has been seen how the coil actuator 1 and the switching device 100 according to the present disclosure allow achieving the intended object offering some improvements over known solutions.

The timing test diagnostic function is implemented in the switching device 100 by coil actuators 1 which provide an easy and economical solution, without specifying other additional or external equipment connected to the switching device 100. Therefore, the solution provided by the present disclosure avoids additional and complex cabling and wiring, extra-costs, and encumbrance into the switching device 100.

Further, a trip circuit supervisor 150 can be advantageously connected to a corresponding coil actuator 1 such that, after the auxiliary contact 103 opens, the coil actuator 1 remains powered to work. Through the trip circuit supervisor 150 is supplied to the counting means 20 (and the comparing means 21, if provided) the power specified to complete the counting operation (and the comparison operation). The coil actuator 1 can be configured for activating the alarm signaling 151 already provided in the trip circuit supervisor 150 for signaling failures in the associated electromagnetic coil 2, so as to signal also undesired conditions of unduly operation long times for closing or opening the switching device 100.

Such results are achieved thanks to a solution which in principle makes the switching device 100 and the coil actuator 1 according to the present disclosure easy to be used in connection with a switchgear. Hence, the present disclosure also encompasses a switchgear including at least a switching device 100 and/or at least a coil actuator 1 according to the present disclosure.

Moreover, all parts/components can be replaced with other technically equivalent elements; in practice, the type of materials, and the dimensions, can be selected as desired.

For example, alternatively to the exemplary embodiment of FIG. 2 the controller 31 can be arranged to directly generate an alarm signaling upon the detection of a counted operation time $T_{open}$ or $T_{close}$ exceeding the predetermined temporal range $T_{range}$.

Alternatively or in addition with respect to the exemplary embodiments previously disclosed, the counted operation time $T_{open}$ or $T_{close}$ can be used to provide information relative to the operative life of the switching device 100, information that is stored and/or displayed through suitable storing and/or displaying means.

Further it is to be understood that the functional blocks in the coil actuator 1 according to present disclosure, e.g., the driving means 10, the counting means 20, the detection means 11, and the comparing means 21, may be all implemented in a single electronic unit through the execution of suitable instructions, or alternatively one or more of such functional block may be implemented by dedicated electronic means and/or units suitably connected each other. For example, the counting means 20 can be implemented by a digital counter 20 triggered by the detection means 11, which in turn may be implemented for example by an electronic circuit including a comparator.

Although the controller 31 has been indicated to be for example a microprocessor, such controller 31 can also be a microcomputer, a minicomputer, a digital signal processor (DSP), an optical computer, a complex instruction set computer, an application specific integrated circuit, a reduced instruction set computer, an analog computer, a digital computer, a solid-state computer, a single-board computer, or a combination of any of these.

Further, instructions, data, signals, and parameters can be delivered to the controller 31 via electronic data carts, manual selection and control, electromagnetic radiation, communication buses, or through any suitable electronic or electrical transfer.

It will therefore be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

We claim:

1. A coil actuator for an associated current switching device which can be actuated during its operation from an open position to a closed position to allow a current flowing therethrough and from said closed position to said open position to interrupt such flowing current, said coil actuator comprising:
   a coil electromagnet arranged to move between a rest position and an actuating position, wherein the movement from the rest position to the actuating position causes the actuation of said switching device,
   wherein said coil actuator includes electronic means arranged to count an operation time ($T_{open}$, $T_{close}$) which is indicative of the duration of said actuation of the switching device.

2. The coil actuator according to claim 1, wherein said electronic means includes:
   detection means arranged to detect a first event and driving means operatively associated to said detection means and operatively connected to said coil electromagnet, said driving means being arranged to electrically drive the coil electromagnet to cause the movement of such coil electromagnet from the rest position to the actuating position upon the detection of said first event by the detection means, said detection means being arranged also to detect a second event which is indicative of the end of the actuation of the switching device; and
   counting means operatively associated to said detection means and arranged to start the counting of said operation time ($T_{open}$, $T_{close}$) when the first event is detected by the detection means and to stop such counting when the second event is detected by the detection means.

3. The coil actuator according to claim 2, wherein said driving means includes a power input circuit arranged to be operatively connected to and receive an input voltage ($V_{in}$) from at least a power source, said detection means being arranged to sense a voltage indicative of said input voltage ($V_{in}$) and to detect a first threshold value ($V_{th\_launch}$) and a second threshold value ($V_{th\_release}$) of such input voltage ($V_{in}$), wherein the detection of said first threshold value ($V_{th\_launch}$) and the detection of said second threshold value ($V_{th\_release}$) correspond to said first event and said second event, respectively.

4. The coil actuator according to claim 3, wherein said counting means are operatively connected to the power input circuit, wherein said power input circuit is arranged to be operatively connected to said at least a power source to continuously receive therefrom at least a minimum input voltage ($V_{in\_min}$) suitable for supplying the counting means.

5. The coil actuator according to claim 4, wherein said comparing means are operatively connected to said power input circuit, wherein said minimum input voltage ($V_{in\_min}$) is suitable for continuously supplying also the comparing means.

6. The coil actuator according to claim 4, wherein said power input circuit is arranged to be operatively connected to a trip circuit supervisor to receive therefrom at least said minimum input voltage ($V_{in\_min}$), said detection means being arranged to detect said minimum input voltage ($V_{in\_min}$) and said driving means being arranged to electrically drive the coil electromagnet to generate a coil supervisor current ($I_{cs}$) flowing through the coil electromagnet when the input voltage ($V_{in}$) is detected to be in a range a between said minimum voltage ($V_{in\_min}$) and said release threshold value ($V_{th\_release}$) by the detection means.

7. The coil actuator according to claim 6, wherein the comparing means are operatively associated with the driving means in that said driving means are arranged to reduce said coil supervisor current ($I_{cs}$) when the comparing means detects that the counted operation time ($T_{open}$, $T_{close}$) exceeds said predetermined temporal range ($T_{range}$).

8. The coil actuator according to claim 3, wherein said detection means are arranged to receive at least one configurable parameter, wherein said at least one configurable parameter includes said first threshold value ($V_{th\_launch}$) and said second threshold value ($V_{th\_release}$).

9. The coil actuator according to claim 2, wherein said driving means are operatively connected to at least one power source to receive power for holding the coil electromagnet in the rest position, and said detection means are arranged to detect the falling of a voltage ($V_{supply}$) generated by said at least one power source below a predetermined undervoltage threshold value, wherein the detection of such voltage falling corresponds to said first event.

10. The coil actuator according to claim 2, wherein said driving means are arranged to apply a configurable delay time between the detection of the first event and the driving of the coil electromagnet.

11. The coil actuator according to claim 2 comprising:
    comparing means operatively associated with said counting means and arranged to compare the counted operation time ($T_{open}$, $T_{close}$) to a predetermined temporal range ($T_{range}$).

12. The coil actuator according to claim 11, wherein said electronic means is configured to generate an alarm signaling when the counted operation time ($T_{open}$, $T_{close}$) exceeds said temporal range ($T_{range}$).

13. The coil actuator according to claim 11, wherein said comparing means are arranged to receive at least one configurable parameter, wherein said at least one configurable parameter includes said temporal range ($T_{range}$).

14. The coil actuator according to claim 2, wherein said electronic means are arranged to provide a continuous power supply to said counting means at least for a time specified to complete the counting operation.

15. The coil actuator according to claim 14, wherein said electronic means are arranged to provide a continuous power supply to said comparing means at least for a time specified to complete the comparison operation.

16. The coil actuator according to claim 15, wherein said counting means and said comparing means are suitable for being operatively connected to energy storage means to receive therefrom the power for completing the counting operation and the comparison operation, respectively.

17. A switching device, comprising at least a coil actuator according to claim 1.

18. The switching device according to claim 17, comprising:
a trip circuit supervisor connected to a power input circuit of the coil actuator, said trip circuit supervisor being configured for detecting the reduction of the current ($I_{tc}$) flowing therethrough below a predetermined threshold, and for generating an alarm signaling upon such detection.

19. A switchgear comprising at least a coil actuator according to claim 1.

20. A switchgear comprising at least a switching device according to claim 19.

* * * * *